United States Patent [19]

Schilling et al.

[11] Patent Number: 5,008,382

[45] Date of Patent: Apr. 16, 1991

[54] CATIONIC AQUEOUS BITUMINOUS EMULSION-AGGREGATE SLURRIES PREPARATION

[75] Inventors: Peter Schilling; Hans G. Schreuders, both of Charleston, S.C.

[73] Assignee: Westvaco Corporation, New York, N.Y.

[21] Appl. No.: 370,052

[22] Filed: Jul. 20, 1989

Related U.S. Application Data

[60] Division of Ser. No. 263,440, Oct. 27, 1988, Pat. No. 4,877,457, which is a continuation-in-part of Ser. No. 197,100, May 20, 1988, Pat. No. 4,810,299.

[51] Int. Cl.$^5$ .................... C08L 95/00; C09D 3/24; B01J 13/00
[52] U.S. Cl. ........................................ 536/11; 536/4.1; 536/18.5; 536/18.6; 527/301; 527/311; 527/312; 106/277; 252/311.5
[58] Field of Search .................... 536/1.1, 4.1, 18.5, 536/18.6; 527/301, 311, 312; 106/277; 252/311.5

[56] References Cited

U.S. PATENT DOCUMENTS

| | | | |
|---|---|---|---|
| 4,478,642 | 10/1984 | Schilling et al. | 106/277 |
| 4,494,992 | 1/1985 | Schilling et al. | 106/277 |
| 4,547,224 | 10/1985 | Schilling | 106/277 |
| 4,597,799 | 7/1986 | Schilling | 106/277 |
| 4,810,299 | 3/1989 | Schilling et al. | 106/277 |
| 4,859,245 | 8/1989 | Schilling et al. | 106/277 |
| 4,859,362 | 8/1989 | Schilling | 106/277 |
| 4,877,457 | 10/1989 | Schilling et al. | 106/277 |

Primary Examiner—Ronald W. Griffin
Attorney, Agent, or Firm—Terry B. McDaniel; Daniel B. Reece, IV; Richard L. Schmalz

[57] ABSTRACT

Cationic aqueous bituminous emulsion-aggregate slurries are disclosed to be formed with cationic emulsions prepared at elevated temperatures by emulsifying bitumen, such as an asphalt, in water with a cation-active emulsifier which is the product of the reaction of a sugar-containing syrup with modified polyamine which is the reaction product of a polyamine with certain polycarboxylic acids and anhydrides.

4 Claims, No Drawings

CATIONIC AQUEOUS BITUMINOUS EMULSION-AGGREGATE SLURRIES PREPARATION

This application is a division of application Ser. No. 07/263,440, filed Oct. 27, 1988, now U.S. Pat. No. 4,877,457 which is a continuation-in-part of application Ser. No. 07,197,100, filed May 20, 1988, now U.S. Pat. No. 4,810,299.

BACKGROUND OF THE INVENTION (1) Field of the Invention

The present invention relates to mixing-grade, quick-setting and slow-setting cationic aqueous bituminous emulsion-aggregate paving slurry seal mixtures. More particularly, this invention relates to said paving slurry seal mixtures formed with cationic emulsions prepared by emulsifying bitumen, such as an asphalt, in water with a cation-active emulsifier which is the product of the reaction of polyamines with certain polycarboxylic acids.

(2) Description of the Prior Art

Conventionally, emulsion slurry seals are formulated from (1) mineral aggregate which is a fine stone aggregate and/or mineral filler and (2) about 15% to about 25% by weight thereof of a mixing-grade, slow-setting emulsion containing from about 50% to about 75% by weight of bituminous residue (usually asphalt), with a further addition of about 5% to about 25% of water, based on the weight of the dry aggregate, to attain slurry consistency. Usually, densely-graded aggregates, such as granite screenings, limestone screenings, dolomite screenings and blast furnace slag, are combined with bituminous emulsions to produce slurry seal compositions. These aggregates range in size from anything passing all through a sieve of No. 4, and even No. 10 mesh, with from 15% to 20% passing through as fine a mesh as 200 mesh, as described in ASTM C136.

The advent of slurry seal as a paving and road maintenance technique was first developed for use with anionic aqueous bituminous emulsions. A slurry seal is an intimate mixture of emulsified bituminous material and fine-grained aggregate held in suitable suspension until applied to the road surface. The slurry seal emulsion must be of an oil-in-water type. In such a mixture with aggregate, the aqueous emulsion form of the bituminous material has been generally preferred because it is less hazardous and more economical to use than hot mix or cutback (solvent containing) asphalts. Further, the aqueous emulsion form can be stored, transported and applied at much lower temperatures, obviating the necessity of heating equipment to maintain a bitumen-aggregate system in a workable or usable form. While these advances have been recognized, widespread acceptance has not been achieved due to disadvantages found in previous aqueous bituminous emulsions.

More recently, cationic bituminous emulsions have come into use and eliminate many of the disadvantages of the anionic emulsions. Bituminous emulsions formulated using cationic emulsifiers do not "break" in the same manner as anionic emulsions, but rather the bituminous material is deposited from the emulsion due to the attraction of polar charges between the bituminous droplets and negatively charged aggregate surfaces. Thus, cationic bituminous emulsions deposit more rapidly than the anionic bituminous emulsions on aggregate surfaces and are bonded to the aggregate by the electrostatic action at the interface of the bitumen and the aggregate material.

The aqueous cationic bituminous emulsions themselves are relatively stable, and the emulsion stability may be enhanced by various additives well known in the art. Most cationic bituminous emulsions, however, deposit on the surface of aggregate materials rapidly when aggregate is contacted with the emulsions. Bitumen from an aqueous cationic bituminous emulsion is deposited from the emulsion due to the charge attraction between the bituminous droplets and the aggregate materials. The rapid setting action of cationic bituminous emulsions is of considerable advantage in road building, such as seal coats, since the roads can be opened to traffic shortly after application of the coating. Although the rate of asphalt deposition, for example, from the emulsion can be controlled to some extent, the time required for complete deposition is never very long and it is therefore the practice to combine the cationic emulsion with the aggregate at the site of road construction, either on the surface of the road itself, or in a mobile mixer which permits the emulsion aggregate mix to be rapidly spread. Due to the charge attraction mechanism, the rapidity of deposition of bituminous materials from the cationic emulsion is closely related to the generally negatively charged surface area of the aggregate or filler material. Thus, while a specific cationic bituminous emulsion might provide suitable properties for use in conjunction with some aggregates, the same cationic emulsion may not exhibit suitable properties when used with very finely ground materials having vastly larger total surface area. The rapid deposition characteristics of the cationic bituminous emulsions frequently makes it impossible to use such emulsions with fine-grained aggregate in slurry form such as in gun application or spreader box application. Therefore, since the slurry seal should mix well, pump well, lay down well, not stiffen while being applied, and, after setting, wear well under traffic, it is particularly desirable to be able to control the setting time of the slurry for various aggregates employed.

Acidified reaction products of the above described polycarboxylic acids, anhydrides, sulfonated fatty acids and epoxidized glycerides with certain polyamines are suitable emulsifiers yielding asphalt emulsions which can be mixed with fine grained aggregate to give workable aggregate/emulsion mixes.

These emulsifiers generally are disclosed in U.S. Pat. No. 4,447,269 to Schreuders, et al., U.S. Pat. No. 4,450,011 to Schilling, et al., U.S. Pat. No. 4,547,224 to Schilling, et al., U.S. Pat. No. 4,462,840 to Schilling, et al., U.S. Pat No. 4,464,286 to Schilling; and U.S. Pat. No. 4,597,799 to Schilling.

However, cationic emulsions produced with the known emulsifiers can only be mixed with aggregates when the temperature of the emulsion or the aggregate is below 100° F. or when the aggregate surfaces are only moderately charged. In hotter climates where the temperature of the mixes are as high as 120° F. and when highly charged aggregates have to be used, these emulsions fail the mixing process.

Accordingly, an object of this invention is to provide novel types of emulsifiers which produce emulsions which can be mixed with aggregate at elevated temperatures.

A further object of this invention is to provide a novel mixture of aggregate and bituminous emulsion.

A further object is to provide a mixture of the above character which is workable under a broad range of conditions.

Another obJect is to provide a mixture of cationic bituminous emulsion and aggregate whose setting time can be varied.

A particular object is to provide an aqueous bituminous emulsion fine-grained aggregate slurry mixture which deposits at a fairly rapid rate after being applied to the surface to be treated, and is usable for a longer period of time to enable application in slurry form.

SUMMARY OF THE INVENTION

The above objectives are met in the cationic aqueous bituminous emulsion-aggregate slurries formed with cationic emulsions prepared by emulsifying bitumen, such as an asphalt, in water with a novel cation-active emulsifier which is the product of the reaction of sugar containing syrups, preferentially molasses, with a modified polyamine prepared by reacting a polyamine with a polycarboxylic acid and anhydrides of the general formulae

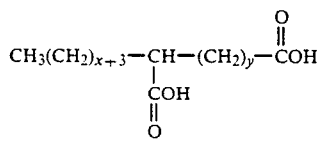

or

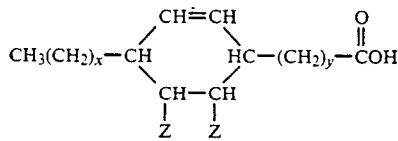

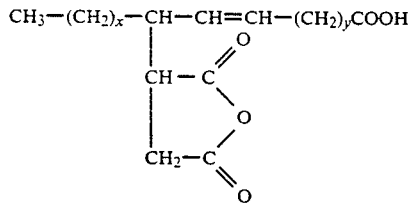

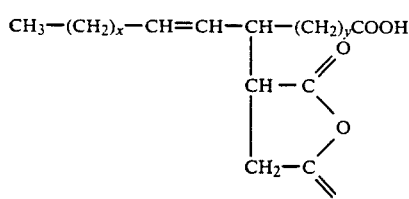

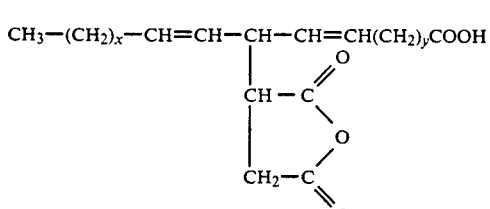

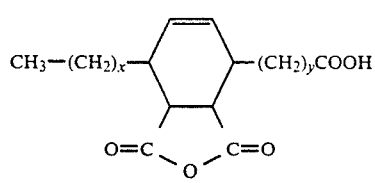

wherein x and y are integers from 3 to 9, x and y together equal 10-14, at least one Z is a carboxylic acid group and any remaining Z is hydrogen.

Additional emulsifiers of this invention are reaction products of sugar containing syrups with modified polyamines prepared by reacting a polyamine with sulfonated fatty acids, with resin acids (rosin) reacted with maleic anhydride or fumaric acid, and epoxidized esters of unsaturated fatty esters such as tallates, oleates, linoleates, and glycerides such as vegetable oils and animal fats. Examples of such reactants include:

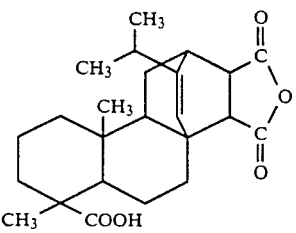

Meleinized Rosin,

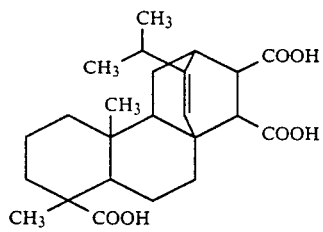

Fumarized Rosin, and

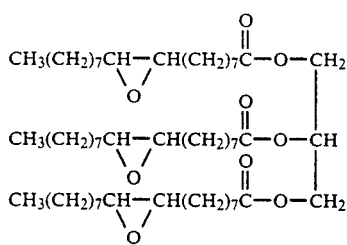

Epoxidized Glyceride

The modified polyamines so formed are the respective amidoamines, imidoamines or imidazolines, which are then reacted with molasses.

DESCRIPTION OF THE PREFERRED EMBODIMENTS

A typical cationic aqueous bituminous emulsion aggregate slurry is formulated in the laboratory with an amount of aggregate pre-wetted with water and mixed with a suitable cationic bituminous emulsion to a desired consistency. Suitable consistency is obtained by using mixed gradations of aggregates forming a smooth non-separating uniform mixture of cationic aqueous bituminous emulsion-aggregate which can be evenly spread onto an existing surface. The ultimate toughness of the applied slurry is obtained as the bitumen, such as asphalt, deposits on the aggregate particles and binds the newly applied coating to the pre-existing surface as a mixture of asphalt cement and aggregate.

As a paving technique at the roadside, a mobile self-propelled unit capable of uniformly metering the aggregate, water, inorganic or organic additive and emulsion components may be used. A typical unit is equipped with separate tanks for aggregate, water, additive and emulsion which are continually metered into a mixing chamber at a pre-determined ratio. The continually fed components are retained in the mixing chamber for approximately one minute and then fed into a spreader box and applied to the surface to be coated. Batch operated pneumatic devices can also be used for suitable placement of the cationic bituminous aggregate slurries of this invention.

The slurry of this invention broadly comprises aggregate and a bituminous emulsion made up of bitumen, water and as cationic emulsifier, the reaction product of a modified polyamine and a polycarboxylic acid as described above in the Summary of Invention.

When the emulsifiers are the reaction products of the modified polyamines with sulfonated carboxylic acids derived by sulfonation of tall oil fatty acid and oleic acid, the sulfonated products are characterized by an acid number from about 220 to 330, saponification number from about 300 to 360.

Sauls and Ruggenberg disclose the sulfonation of oleic acid with sulfur trioxide in liquid sulfur dioxide in U.S. Pat. No. 2,743,288.

Pugh and Chesworth disclose in British Pat. No. 1,278,421 the sulfonation of oleic acid with gaseous sulfur trioxide diluted with an inert gas with a continuously formed liquid film of the unsaturated fatty acid.

The sulfonation of tall oil fatty acid is also disclosed in the above mentioned patents. Because of the complexity of the composition of tall oil fatty acids, no attempt to identify the sulfonated products was made.

Reaction mechanism and all aspects of sulfonation are reviewed in E. E. Gilbert, "Sulfonation and Related Reactions," R. E. Krieger Publishing Company, Huntington, N.Y., 1977.

Molasses, is a by-product of the sugar industry; it is the mother liquor remaining after crystallization and removal of sucrose from the juices of sugar cane or sugar beet and is used a variety of food and non-food applications.

| Molasses Type | Solids % | Total Sugars as Invert wt % | Crude Protein % | Total Ash wt % |
|---|---|---|---|---|
| Cane (Louisiana) | 80.8 | 59.5 | 3.0 | 7.2 |
| Cane (Refiner's) | 75.4 | 55.9 | 2.1 | 8.6 |
| High Test (Cuba) | 80.4 | | 0.7 | 1.4 |
| Beet (Wisconsin) | 78.6 | 52.7 | 11.4 | 9.3 |
| Corn | 74.9 | 50.3 | 0.4 | 8.9 |
| Citrus | 71.4 | 42.4 | 4.7 | 4.8 |

Raw sugar is produced from sugarcane by a process that involves extraction of the sugar in water, treatment to remove impurities, concentration, and several crystallizations. After the first crystallization and removal of "first sugar," the mother liquor is called first molasses. First molasses is recrystallized to obtain a second lower quality sucrose (second sugar) and a second molasses. After a third crystallization, the third molasses contains considerable nonsucrose material, and additional recovery of sucrose is not economically feasible. The third molasses is sold as blackstrap, final, or cane molasses. Raw sugar obtained from the above process is mixed with water to dissolve residual molasses and separated by centrifugation. This process is called affination and the syrup is referred to as affination liquor. The sugar is dissolved in water, treated to remove color and impurities, and subjected to several crystallizations to obtain refined sugar. The mother liquor from the final crystallization is combined with affination liquor and crystallized to produce a dark sugar ("remelts") which is recycled to raw sugar. The remaining mother liquor is called refiners molasses and is similar to final molasses but usually of better quality.

Molasses composition depends on several factors, e.g., locality, variety, soil, climate, and processing. Cane molasses is generally at pH 5.5-6.5 and contains 30-40 wt. % sucrose and 15-20 wt. % reducing sugars. Beet molasses is ca. pH 7.5-8.6 and contains ca. 50-60 wt. % sucrose, a trace of reducing sugars, and 0.5-2.0 wt. % raffinose.

Another source of molasses is "wood molasses" obtained by acid hydrolysis of lignocellulosic matter pertained in wood, specifically in hardwood of deciduous trees.

Molasses has been treated with ammonia resulting in a mix of heterocyclic substances mostly consisting of pyrazines and imidazoles. A general description of the chemistry of sucrose and molasses can be found in "Sucrose Chemicals, A critical review of a quarter-century of research by the Sugar Research Foundation" by Valerie Kollonitsch, C. H. Kline & Company, Inc., The International Sugar Research Foundation, Inc., 1970.

The reaction of molasses or dextrose with polyethylene amine is not known to have been described in the literature. The reaction of dextrose with amino acids or proteins yields products which form pigments of high molecular weights (Maillard reaction).

Polyamines suitable for modification prior to reaction with the syrup are those which are able to form imidazolines or amidoamines with carboxylic acids such as ethylene diamine, diethylene triamine, triethylene tetramine, tetraethylene pentamine, pentaethylene hexamine, and higher homologues; N-aminoethyl propane diamine, N,N'-diaminoethyl propane diamine and the N-aminoethyl- or N,N'-diaminoethyl-substituted butane diamines, pentane diamines and hexane diamines, and N-hydroxy ethyl ethylene diamine. These compounds have the general formula

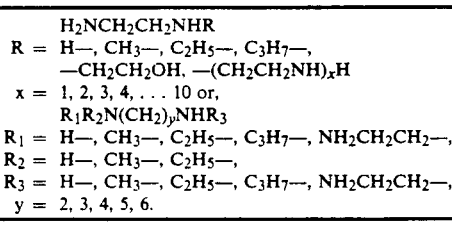

Amines capable of forming amidoamines but not imidazolines are: 1,3-diaminopropane, 1,4-diaminobutane, 1,5-diaminopentane, 1,6-diaminohexane, piperazine (1,4-diazacyclohexane), N-aminoethylpiperazine, N-hydroxyethyl piperazine, N-aminopropyl-propane diamine-1,3, N-methyl-N-aminopropylpropane diamine-1,3, N-aminohexylhexane diamine-1,6.

In addition, polyamines containing other functionalities such as (—O—) thioether (—S—), sulfoxide (—SO—), sulfone (—SO$_2$—) groups, as well as aromatic structures are also suitable for condensation.

$$R_1H_2N(CH_2)_xY(CH_2)_zNH_2$$

Y=O, S, SO, SO$_2$, C$_6$H$_5$—
x=2–10
Y=2–10

Cationic surface active materials with similar properties can also be prepared by first reacting a fatty acid, fatty ester such as animal fat or oils (glycerides), or resin acid (rosin) or their derivatives obtained by reaction with acrylic acid, metacrylic acid, fumaric acid, maleic anhydride, epoxidizing agents such as peracetic acid or perbenzoic acid or by sulfonation as described earlier with a suitable polyamine listed above and then reacting the intermediates obtained molasses in aqueous solution or without water present.

Further modification of the above described polyamino amidoamines are their reaction products with reactive oxirane systems such as ethylene oxide, propylene oxide or butylene oxide. Reaction occurs initially on primary and secondary nitrogens, that is, a nitrogen to which one or two hydrogen atoms are covalently bound. The reaction products belong to the class of N-hydroxyethyl-, N-2-hydroxypropyl- and N-2-hydroxy butyl -amino amidoamines. If excess oxirane is reacted, polyethylene oxides, polypropylene oxides or polybutylene oxides are obtained. The hydroxyl groups will also react in this case.

Another modification may involve the use of an alkylating agent such as methyl-, ethyl-, or benzyl halides, sulfates, phosphates, etc. The resulting compounds are classified as mono-, di-, or triquaternary ammonium salts. Their main characteristic is their solubility in aqueous systems without addition of acid, as is the case with amines, amidoamines. The use of reactive products of polyamino amidoamines with the above described C$_{19}$-, C$_{21}$-, C$_{22}$-polycarboxylic acid and anhydrides as well as with maleinized or fumarized (rosin) resin acids, sulfonated fatty acids or epoxidized glycerides as asphalt emulsifiers, and specifically as emulsifiers for solventless asphalt emulsions and emulsions for slurry seal applications, was heretofore unknown.

The examples which follow are illustrative of emulsifiers used to obtain cationic asphalt in water emulsions eminently useful for mixing under shear with a variety of siliceous and calcareous aggregates. After setting (evaporation of water), the asphalt films show excellent adhesion to the aggregate surface.

In preparing the bituminous emulsions employed in the invention paving slurry seal mixtures, an aqueous acidic solution of the emulsifiers described below is intimately mixed under high shear in a colloid mill. The bitumen content can range from 30% to about 80% by weight, preferably between 60% and 70%. The dosage of the emulsifier can range from 0.1–10% by weight of the emulsion, preferably between 0.5–2% by weight of the emulsion. Dependent on the emulsifier, a slurry grade emulsion is obtained in a pH range of 2–7, with the optimum performance at a pH of about 2.5.

The "bitumen" used in the emulsion may be derived from domestic or foreign crude oil; it also includes bitumen, natural asphalt, petroleum oil, oil residue of paving grade, plastic residue from coal tar distillation, petroleum pitch, and asphalt cements diluted from solvents (cutback asphalts). Practically any viscosity or penetration graded asphalt cement for use in pavement construction as described in ASTM designation D-3381 and D-946 may be emulsified with the aid of the emulsifiers of this invention.

The cationic soap solutions are normally obtained by suspending the amidoamine or imidazoline in water to which a sufficient amount of a suitable acid, for instance, hydrochloric, sulfuric, and phosphoric acid or the like is added until the desired pH value below 7 is reached and a clear emulsifier solution is obtained. Thereafter, the soap solution which is preheated to 55° C. and the fluid asphalt which is preheated to 120–125° C. are mixed under high shear in a colloid mill to give asphalt emulsions of brown color and creamy texture. Prior to testing according to ASTM D-244, the emulsions are stored at 70° C. for 16 hours.

The aggregates of the invention paving slurry seal mixtures are densely graded aggregates which range in size from anything passing through a No. 4 sieve and at least 80% retained on 200 mesh.

Aggregate mixing tests are performed by mixing the aggregate with water and aqueous bituminous emulsion. An inorganic additive-mineral filler, such as portland cement, hydrated lime, limestone dust and fly ash, may be added to accelerate set/break time and organic salts, such as ammonium sulfate, or emulsifiers may be added to retard the set/break of the slurry system. Such additives shall comply with the requirements of ASTM D-242. The materials are mixed in a mixing bowl until a homogeneous slurry mixture is obtained. The inability to form a stable slurry within 3 to 4 minutes of mixing time when proper proportions of each ingredient are used would indicate a mixture in which the materials are not compatible. This mix design is necessary to simulate field conditions. After the slurry is mixed, it is spread in a mold which is placed on an asphalt felt, and the set/break time is measured by blotting the exposed slurry surface with a paper towel, the slurry is considered to be "set." The cure time could also be measured with a cohesion testing device. Many other tests such as described in ASTM D-3910 are used to measure strength and other physical properties of slurry. The Performance Guide for Slurry Seal published by the Asphalt Emulsion Manufacturers Association is used to measure the performance of the slurry seal.

The emulsion should be stable during mixing and should set within the designed time period following application. The emulsifiers of this invention perform very satisfactorily without auxiliary emulsifiers. For instance, the setting times can be controlled with the concentration of emulsifier, the addition of lime, cement or other inorganic additive or an organic additive, which would alter the break characteristics of the slurry system. An organic additive-polymer latex may also be employed to strengthen the matrix. The organic additive is preferably added to the emulsion-aggregate slurry.

Either a mixture of tall oil fatty acids, preferably tall oil pitch, can be added to the bitumen (asphalt) prior to emulsification to improve break or improve the viscosity of the emulsion, or blends of the above described amidoamines with compatible cationic or nonionic emulsifiers may be used for the emulsification of the bitumen. Auxiliary emulsifiers, which may constitute up to 90% of the total combined emulsifier formulation, are fatty amines, fatty propane diamines, fatty amidoamines, and fatty imidazolines. Others are fatty monoquaternary ammonium salts and fatty diquaternary diammonium salts and nonionic emulsifiers, such as ethylene glycol polyethers or nonyl- or dodecyl phenol. Combinations of amidoamines based on fatty monocarboxylic acids, of various sources and the $C_{19}$- and $C_{21}$-dicarboxylic acids or $C_{22}$-tricarboxylic acid or anhydrides disclosed in this invention can also be obtained by reacting the modified polyamines with a blend of fatty monocarboxylic acids and di- or tricarboxylic acids or anhydrides. Monocarboxylic acids suitable for this purpose are tall oil fatty acids, crude tall oil, rosin acids, tall oil pitch, tallow fatty acids, soya fatty acids and the like. Kraft lignin, oxidized lignin, desulfonated sulfite lignin or VINSOL may also be co-reacted.

Dimer acids, which are long chain $C_{36}$-aliphatic carboxylic acids obtained by dimerization of fatty acids of various sources, may be also co-reacted. An example of this type of acid is produced by Emery Industries, Inc. under the trade name "Empol ® Dimer Acids."

In a similar way, blends of sulfonated fatty acids as well as fumarized or maleinized rosin (resin acids) or epoxidized glycerides or other esters, with the above described co-reactants (fatty acids, oils, fats, lignins, VINSOL, dimer acid) can be reacted with the modified polyamines to give combinations of polyamidoamines.

The emulsions prepared with these polyaminoamide-molasses condensates disclosed in this invention are stable and can be stored for a long period of time until required for use. The cationic aqueous bituminous emulsions employed in the invention slurries are slow-setting, mixing grade slurries under ASTM D-2397; however, the set time may be shortened by adding lime or cement, providing an emulsion with quick-setting characteristics.

General Method of the Preparation of Molasses Condensates:

To 100 parts of the reaction product of a $C_8$–$C_{22}$ fatty acid with a polyalkylene amine where the fatty acid residue can be saturated or containing one or more C=C double bonds, 10–500 parts of 80% molasses are added and heated for 2–16 hours at from 60° to 100° C. To ensure homogeneity of the reaction mixture, alcohols such as i-propanol and ethylene glycol may be added.

Blends of 100 parts of the fatty nitrogen compounds with 10–50 parts molasses can be heated to 160°–220° C. to form high temperature condensates of complex composition.

In addition to the $C_8$–$C_{22}$ fatty amine compounds, the amidoamines, imidoamine amines, di-imidazolines, amidoamine/imidazoline, or polyamidoamines of the reaction products of polyamine and a member of the group consisting of unsaturated fatty acids, esters, glycerides with acrylic acid, metacrylic acid, fumaric acid and maleic anhydride, sulfur trioxide, or peracetic acid as well as the corresponding nitrogen derivatives of resin acids (rosin), maleinized, fumarized, or acrylated resin acids are used as reactants with the molasses.

The practice of this invention may be seen in the following examples wherein the preparation of various types of emulsifiers and types of slurries of the invention is described.

Example 1

This example gives the procedure for particular invention emulsifiers:

Emulsifier A

To 100 g of a polyamine blend with the average molecular weight 140, 100 g of $C_{21}$-dicarboxylic acid (DIACID 1550 ®) was added and heated to 240° C. After all the condensate was collected, it was cooled.

Emulsifier B

To 280 g tall oil fatty acid (L-5), 100 g maleic anhydride and 0.5 g of iodine was added and heated to 200° C. for three hours. It was cooled to 180° C. and 100 g of ethylene glycol added and cooled to 80° C. At this temperature, 330 g of polyamine blend with the average molecular weight 140 was added and heated to 220° C. After all the distillate was collected, it was cooled to room temperature.

Emulsifier C

To 100 g Emulsifier B, 50 g of 80% molasses was added and heated at 90° C. for 16 hours.

Emulsifier D

This emulsifier was prepared in the same manner as Emulsifier B, but instead of 100 g maleic anhydride, 50 g maleic anhydride was used.

Emulsifier E

To 100 g Emulsifier D, 50 g of 80% molasses was added and heated at 90° C. for 16 hours.

Emulsifier F

This emulsifier was prepared in the same manner as Emulsifier B. Instead of tall oil fatty acid (L-5), tall oil fatty acid 1483, mainly consisting of oleic acid and elaidic acid, was used.

Emulsifier G

To 100 g Emulsifier F, 50 g of 80% molasses was added and heated at 90° C. for 16 hours.

Example 2

A cationic aqueous bituminous emulsion was prepared employing each of the emulsifiers of Example 1 and aggregate mixing tests with each emulsion as previously performed.

First, cationic emulsions were prepared with either 62–64% Exxon ® asphalt or Edgington Oil ® AC 20 asphalt, 1.5–1.75% emulsifier at pH 2.5 (adjusted with hydrochloric acid) and water to make up 100% (percentages based on the weight of the emulsion). See Table I.

Next, slurries were prepared by adding one 100 g of Camak (Georgia) granite screenings, or Sahuaro (Arizona) aggregate, 16% of the cationic aqueous bituminous emulsion, 14% water and either 0% or 0.5% stucco, (Plaster of Paris, calcium sulfate hemihydrate) as mixing aid (percentages based on the weight of the aggregate). See Table II.

The mixing experiments were carried out by keeping the temperature of the emulsion, water and aggregate at 120° F. and 80° F. (cold), respectively, as indicated in the table.

This example illustrates the improved high temperature mixing performance and coating ability of emulsions prepared with molasses condensates as compared with commercial cationic slurry seal emulsifiers.

The slurry set times were determined by the test procedures previously described, i.e., by blotting with a paper towel the exposed surface of the slurry spread in mold on an asphalt felt. It no brown is transferred to the paper, the slurry is considered set.

Also, this example shows the improved high temperature mixing performance of aqueous bituminous emulsions prepared with the described emulsifiers.

Example 3

This example illustrates the improved high temperature mixing performance and coating ability of molasses condensates prepared with commercial cationic slurry seal emulsifiers as seen in Table III (Exxon Asphalt, Camak Aggregate) and Table IV (Edgington Hard Base, Camak and Sahuaro Aggregates).

The slurry set times were determined by the test procedures previously described, i.e., by blotting with a

TABLE I

Evaluation of Cationic Slurry Seal Emulsifiers with Exxon Asphalt, pH 2.5, 64% Asphalt Content and Camak Aggregate

| Emulsifier | Mixing Performance[a] | | | | Set Time (min) | % Coating[c] |
|---|---|---|---|---|---|---|
| | % Dosage | Temperature | % Additive[b] | Comments | | |
| Emulsifier A | 1.5 | 120° F.[d] | | Broke in 5 secs. | | |
| | | Cold | | Broke in 50 secs. | | |
| Emulsifier B | 1.5 | 120° F.[d] | 0.5 Stu | Flow poor | 40+ | 95 |
| | | | | Flow excellent | 60+ | 90 |
| | | 120° F.[d] | 0.5 Stu | Flow good | 60+ | 95 |
| | | | | Flow excellent | 60+ | 95 |
| Emulsifier C | 1.5 | 120° F.[d] | 0.5 Stu | Broke in 30 secs. | | |
| | | | | Flow excellent | 60+ | 100 |
| | | 120° F.[d] | 0.5 Stu | Flow excellent | 60+ | 90 |
| | | | | Flow excellent | 60+ | 95 |

[a]100 parts aggregate, 10 parts water and 16 parts emulsion were used for the mixing experiments.
[b]Based on the weight of the aggregate; Stu: Stucco, Plaster of Paris Ca-sulfate hemihydrate.
[c]After boiling in water for 10 minutes.
[d]Emulsion was tested immediately after it was prepared.

TABLE II

Evaluation of Cationic Slurry Seal Emulsifiers with Edgington Hard Base, pH 2.5, 64% Asphalt Content and Camak Aggregate

| Emulsifier | Mixing Performance[a] | | | | Set Time (min) | % Coating[c] |
|---|---|---|---|---|---|---|
| | % Dosage | Temperature | % Additive[b] | Comments | | |
| Emulsifier A | 1.5 | 120° F. | | Broke in 5 secs. | | |
| Emulsifier D | 1.75 | 120° F. | | Broke in 30 secs. | | |
| | | Cold | | Flow excellent | 60+ | 95 |
| Emulsifier E | 1.75 | 120° F. | | Flow excellent | 60+ | 95 |
| | | Cold | | Flow excellent | 60+ | 92 |
| Emulsifier F | 1.75 | 120° F. | | Flow fair | 60+ | 98 |
| | | Cold | | Flow excellent | 60+ | 90 |
| Emulsifier G | 1.75 | 120° F. | | Flow excellent | 60+ | 95 |
| | | Cold | | Flow excellent | 60+ | 95 |

[a]100 parts aggregate, 10 parts water and 16 parts emulsion were used for the mixing experiments.
[b]Based on the weight of the aggregate; C: Cement.
[c]After boiling in water for 10 minutes.

paper towel the exposed surface of the slurry spread in mold on an asphalt felt. If no brown is transferred to the paper, the slurry is considered set.

TABLE III

Evaluation of Cationic Slurry Seal Emulsifiers with Exxon Asphalt; pH 2.5; 64.0% Asphalt Content and Camak Aggregate

| Emulsifier | Mixing Performance[a] | | | | Set Time (min) | % Coating[c] |
|---|---|---|---|---|---|---|
| | % Dosage | Temperature | % Additive[b] | Comments | | |
| Catamine 101 | 1.7 | 120° F. | .5 Stu | Broke in 5 secs. | | |
| | | 120° F. | | Broke in 5 secs. | | |
| | | Cold | .5 Stu | Broke in 5 secs. | | |
| | | Cold | | Flow very poor | 20 | 90 |
| Catamine 102 | 1.7 | 120° F. | .5 Stu | Broke in 5 secs. | | |
| | | 120° F. | | Broke in 5 secs. | | |

TABLE III-continued

Evaluation of Cationic Slurry Seal Emulsifiers with Exxon Asphalt; pH 2.5; 64.0% Asphalt Content and Camak Aggregate

| Emulsifier | % Dosage | Mixing Performance[a] Temperature | % Additive[b] | Comments | Set Time (min) | % Coating[c] |
|---|---|---|---|---|---|---|
| | | Cold | .5 Stu | Broke in 5 secs. | | |
| | | Cold | | Flow poor | 20 | 100 |
| INDULIN MQK-1M | 1.7 | 120° F. | .5 Stu | Broke in 5 secs. | | |
| | | 120° F. | | Broke in 5 secs. | | |
| | | Cold | .5 Stu | Broke in 20 secs. | | |
| | | Cold | | Flow poor | 30 | 100 |
| INDULIN MQK-1M-Molasses[d] (100:60) | 1.7 | 120° F. | .5 Stu | Broke in 5 secs. | | |
| | | 120° F. | | Flow excellent | 60+ | 100 |
| | | Cold | .5 Stu | Broke in 5 secs. | | |
| | | Cold | | Flow excellent | 60+ | 100 |
| INDULIN | 1.5 | 120° F. | .5 Stu | Broke in 5 secs. | | |
| | | 120° F. | | Broke in 5 secs. | | |
| | | Cold | .5 Stu | Broke in 40 secs. | | |
| | | Cold | | Flow poor | | |
| INDULIN MQK[e]-Molasses[d] (100:25) | 1.5 | 120° F. | .5 Stu | Broke in 5 secs. | | |
| | | 120° F. | | Flow excellent | 60+ | 98 |
| | | Cold | .5 Stu | Flow excellent | 60+ | 96 |
| | | Cold | | Flow excellent | 60+ | 100 |
| INDULIN MQK[e]-Molasses[d] (100:50) | 1.5 | 120° F. | .5 Stu | Broke in 30 secs. | | |
| | | 120° F. | | Flow excellent | 60+ | 100 |
| | | Cold | .5 Stu | Flow excellent | 60+ | 95 |
| | | Cold | | Flow excellent | 60+ | 95 |
| Akzo Redicote 5762 | 1.7 | 120° F. | .5 Stu | Broke in 5 secs. | | |
| | | 120° F. | | Broke in 10 secs. | | |
| | | Cold | .5 Stu | Flow fair | 60+ | 60 |
| | | Cold | | Flow excellent | 60+ | 55 |
| Akzo Redicote 4868 | 1.7 | 120° F. | .5 Stu | Flow excellent | 60+ | 60 |
| | | 120° F. | | Flow excellent | 60+ | 60 |
| | | Cold | .5 Stu | Flow excellent | 60+ | 50 |
| | | Cold | | Flow excellent | 60+ | 50 |
| Akzo Redicote E-11 | 1.7 | 120° F. | .5 Stu | Broke in 5 secs. | | |
| | | 120° F. | | Flow poor | 60+ | 95 |
| | | Cold | .5 Stu | Flow fair | 60+ | 90 |
| | | Cold | | Flow excellent | 60+ | 95 |

[a]100 parts aggregate, 10 parts water and 16 parts emulsion were used for the mixing experiments.
[b]Based on the weight of the aggregate; Stu: Stucco, Plaster of Paris.
[c]After boiling in water for 10 minutes.
[d]80% solids in water; heated five hours at 90° C.
[e]80% active.

TABLE IV

Evaluation of Cationic Slurry Seal Emulsifiers
Edgington Hard Base, pH 2.5; 64.0% Asphalt Content,
Camak and Sahuaro Aggregates

| Emulsifier | % Dosage | Aggregate | Mixing Performance[a] | | | Set Time (min) | % Coating[c] |
|---|---|---|---|---|---|---|---|
| | | | Temperature | % Additives[b] | Comments | | |
| INDULIN MQK-1M | 1.7 | Sahuaro | 120° F. | .5 Stu | Broke in 5 secs. | | |
| | | | 120° F. | | Broke in 5 secs. | | |
| | | | Cold | .5 Stu | Broke in 25 secs. | | |
| | | | Cold | | Broke in 50 secs. | | |
| | | Camak | Cold | .5 Stu | Broke in 55 secs. | | |
| | | | Cold | .5 Stu | Flow excellent | 60+ | 100 |
| INDULIN MQK-1M-Molasses[d] (100:30) | 1.7 | Sahuaro | 120° F. | .5 Stu | Broke in 5 secs. | | |
| | | | 120° F. | | Broke in 20 secs. | | |
| | | | Cold | .5 Stu | Broke in 20 secs. | | |
| | | | Cold | | Broke in 30 secs. | | |
| | | Camak | Cold | | Flow poor | 60+ | 95 |
| | | | Cold | | Flow excellent | 60+ | 95 |
| INDULIN MQK[e] | 1.7 | Sahuaro | 120° F. | .5 Stu | Broke in 5 secs. | | |
| | | | 120° F. | | Broke in 10 secs. | | |
| | | | Cold | .5 Stu | Broke in 20 secs. | | |
| | | | Cold | | Broke in 20 secs. | | |
| | | Camak | Cold | .5 Stu | Flow excellent | 60+ | 100 |
| | | | Cold | | Flow fair | 20 | 100 |
| INDULIN MQK[e]-Molasses[d] (100:25) | 1.7 | Sahuaro | 120° F. | .5 Stu | Broke in 10 secs. | | |
| | | | 120° F. | | Broke in 10 secs. | | |
| | | | Cold | .5 Stu | Broke in 55 secs. | | |
| | | | Cold | | Broke in 25 secs. | | |
| | | Camak | Cold | .5 Stu | Flow excellent | 60+ | 55 |
| | | | Cold | | Flow excellent | | |
| Akzo Redicote 5762 | 1.7 | Sahuaro | 120° F. | .5 Stu | Broke in 5 secs. | | |
| | | | 120° F. | | Broke in 5 secs. | | |
| | | | Cold | | Broke in 5 secs. | | |
| | | | Cold | | Broke in 5 secs. | | |
| | | Camak | Cold | .5 Stu | Flow excellent | 60+ | 50 |
| | | | Cold | | Flow excellent | | |
| Akzo Redicote 4868 | 1.7 | Sahuaro | 120° F. | .5 Stu | Broke in 5 secs. | | |
| | | | 120° F. | | Broke in 5 secs. | | |
| | | | Cold | .5 Stu | Broke in 5 secs. | | |
| | | | Cold | | Broke in 5 secs. | | |
| | | Camak | Cold | .5 Stu | Flow excellent | 60+ | 50 |
| | | | Cold | | Flow excellent | 60+ | 50 |
| Akzo Redicote E-11 | 1.7 | Sahuaro | 120° F. | .5 Stu | Broke in 5 secs. | | |
| | | | 120° F. | | Broke in 5 secs. | | |

TABLE IV-continued
Evaluation of Cationic Slurry Seal Emulsifiers
Edgington Hard Base, pH 2.5; 64.0% Asphalt Content,
Camak and Sahuaro Aggregates

| Emulsifier | Mixing Performance[a] | | | | | Set Time (min) | % Coating[c] |
|---|---|---|---|---|---|---|---|
| | % Dosage | Aggregate | Temperature | % Additives[b] | Comments | | |
| | | | Cold | | Broke in 5 secs. | | |
| | | | Cold | | Broke in 5 secs. | | |
| | | Camak | Cold | | Flow excellent | 60+ | 95 |
| | | | Cold | | Flow excellent | 60+ | 95 |

[a]100 parts aggregate, 10 parts water and 16 parts emulsion were used for the mixing experiments.
[b]Based on the weight of the aggregate; Stu: Stucco, Plaster of Paris, Ca-sulfate hemihydrate.
[c]After boiling for 10 min. in water.
[d]80% solids in water; heated five hours at 90° C.
[e]80% active.

While the invention has been described and illustrated herein by references to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. A composition of matter obtained by (1) modifying a polyamine by reaction with a member of the group consisting of sulfonated fatty acids, resin acids (rosin) reacted with maleic anhydride or fumaric acid, and epoxidized esters of unsaturated fatty esters from the group consisting of tallates, oleates, linoleates, glycerides, and polycarboxylic acids and their anhydrides of the formulae

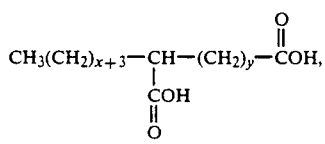

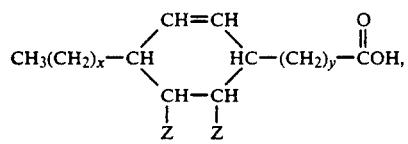

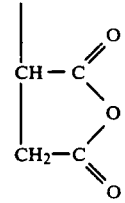

-continued

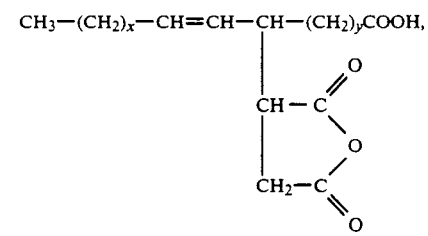

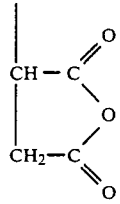

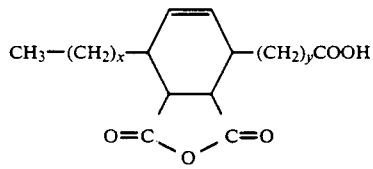

wherein x and y are integers from 3 to 9, x and y together equal 10–14, at least one Z is a carboxylic acid group and any remaining Z is hydrogen and (2) reacting the modified polyamine with a sugar-containing syrup.

2. The composition of matter of claim 1 wherein the modified polyamine is co-reacted with kraft lignin, desulfonated lignosulfonates, or dimerized fatty acids.

3. The composition of matter of claim 2 wherein the dimerized fatty acids include $C_{36}$-dimer acid.

4. The composition of matter of claim 1 wherein the syrup is molasses.

* * * * *

UNITED STATES PATENT AND TRADEMARK OFFICE
CERTIFICATE OF CORRECTION

PATENT NO.   : 5,008,382
DATED        : April 16, 1991
INVENTOR(S)  : Schilling et al.

It is certified that errors appear in the above-identified patent and that said Letters Patent is hereby corrected as shown below:

In column 1, line 9, delete "07,197,100" and substitute therefor --07/197,100--.

In column 3, line 4, delete "obJect" and substitute therefor --object--.

In column 4, line 32, delete "Meleinized" and substitute therefor --Maleinized--.

In column 5, line 49, after used, insert --in--.

In column 13, Table III, below the third occurrence of INDULIN, insert --MQK$^{(e)}$--.

Replace Tables III and IV with the attached Tables III and IV. The positioning of the % Additive .5 Stu is wrong throughout both tables in the patent.

Signed and Sealed this

Twenty-fifth Day of January, 1994

Attest:

BRUCE LEHMAN

Attesting Officer          Commissioner of Patents and Trademarks

TABLE III

Evaluation of Cationic Slurry Seal Emulsifiers
with Exxon Asphalt; pH 2.5; 64.0% Asphalt Content
and Camak Aggregate

| Emulsifier | % Dosage | Mixing Performance[a] Temperature | % Additive[b] | Comments | Set Time (min) | % Coating[c] |
|---|---|---|---|---|---|---|
| Catamine 101 | 1.7 | 120°F | | Broke in 5 secs. | | |
| | | 120°F | .5 Stu | Broke in 5 secs. | | |
| | | Cold | | Broke in 5 secs. | | |
| | | Cold | .5 Stu | Flow very poor | 20 | 90 |
| Catamine 102 | 1.7 | 120°F | | Broke in 5 secs. | | |
| | | 120°F | .5 Stu | Broke in 5 secs. | | |
| | | Cold | | Broke in 5 secs. | | |
| | | Cold | .5 Stu | Flow poor | 20 | 100 |
| INDULIN MQK-1M | 1.7 | 120°F | | Broke in 5 secs. | | |
| | | 120°F | .5 Stu | Broke in 5 secs. | | |
| | | Cold | | Broke in 20 secs. | | |
| | | Cold | .5 Stu | Flow poor | 30 | 100 |
| INDULIN MQK-1M-Molasses[d] (100:60) | 1.7 | 120°F | | Broke in 5 secs. | | |
| | | 120°F | .5 Stu | Flow excellent | 60+ | 100 |
| | | Cold | | Broke in 5 secs. | | |
| | | Cold | .5 Stu | Flow excellent | 60+ | 100 |
| INDULIN MQK[e] | 1.5 | 120°F | | Broke in 5 secs. | | |
| | | 120°F | .5 Stu | Broke in 5 secs. | | |
| | | Cold | | Broke in 40 secs. | | |
| | | Cold | .5 Stu | Flow poor | | |

TABLE III
(continued)

Evaluation of Cationic Slurry Seal Emulsifiers
with Exxon Asphalt; pH 2.5; 64.0% Asphalt Content
and Camak Aggregate

| Emulsifier | Mixing Performance[a] | | | Comments | Set Time (min) | % Coating[c] |
| | % Dosage | Temperature | % Additive[b] | | | |
|---|---|---|---|---|---|---|
| INDULIN MQK[e]- Molasses[d] (100:25) | 1.5 | 120°F | | Broke in 5 secs. | | |
| | | 120°F | .5 Stu | Flow excellent | 60+ | 98 |
| | | Cold | - | Flow excellent | 60+ | 96 |
| | | Cold | .5 Stu | Flow excellent | 60+ | 100 |
| INDULIN MQK[e]- Molasses[d] (100:50) | 1.5 | 120°F | | Broke in 30 secs. | | |
| | | 120°F | .5 Stu | Flow excellent | 60+ | 100 |
| | | Cold | | Flow excellent | 60+ | 95 |
| | | Cold | .5 Stu | Flow excellent | 60+ | 95 |
| Akzo Redicote 5762 | 1.7 | 120°F | | Broke in 5 secs. | | |
| | | 120°F | .5 Stu | Broke in 10 secs. | | |
| | | Cold | | Flow fair | 60+ | 60 |
| | | Cold | .5 Stu | Flow excellent | 60+ | 55 |
| Akzo Redicote 4868 | 1.7 | 120°F | | Flow excellent | 60+ | 60 |
| | | 120°F | .5 Stu | Flow excellent | 60+ | 60 |
| | | Cold | | Flow excellent | 60+ | 50 |
| | | Cold | .5 Stu | Flow excellent | 60+ | 50 |

TABLE III
(continued)

Evaluation of Cationic Slurry Seal Emulsifiers
with Exxon Asphalt; pH 2.5; 64.0% Asphalt Content
and Camak Aggregate

| Emulsifier | Mixing Performance(a) | | | Comments | Set Time (min) | % Coating(c) |
|---|---|---|---|---|---|---|
| | % Dosage | Temperature | % Additive(b) | | | |
| Akzo Redicote E-11 | 1.7 | 120°F | | Broke in 5 secs. | | |
| | | 120°F | .5 Stu | Flow poor | 60+ | 95 |
| | | Cold | | Flow fair | 60+ | 90 |
| | | Cold | .5 Stu | Flow excellent | 60+ | 95 | a) 100 parts aggregate, 10 parts water and 16 parts emulsion were used for the mixing experiments.
b) Based on the weight of the aggregate; Stu: Stucco, Plaster of Paris.
c) After boiling in water for 10 minutes.
d) 80% solids in water; heated five hours at 90°C.
e) 80% active.

TABLE IV

Evaluation of Cationic Slurry Seal Emulsifiers
Edgington Hard Base, pH 2.5; 64.0% Asphalt Content,
Camak and Sahuaro Aggregates

| Emulsifier | % Dosage | Mixing Performance(a) Aggregate | Temperature | % Additives(b) | Comments | Set Time (min) | % Coating(c) |
|---|---|---|---|---|---|---|---|
| INDULIN MQK-1M | 1.7 | Sahuaro | 120°F | | Broke in 5 secs. | | |
| | | | 120°F | .5 Stu | Broke in 5 secs. | | |
| | | | Cold | | Broke in 25 secs. | | |
| | | | Cold | .5 Stu | Broke in 50 secs. | | |
| | | Camak | Cold | .5 Stu | Broke in 55 secs. | | |
| | | | Cold | .5 Stu | Flow excellent | 60+ | 100 |
| INDULIN MQK-1M- Molasses(d) (100:30) | 1.7 | Sahuaro | 120°F | | Broke in 5 secs. | | |
| | | | 120°F | .5 Stu | Broke in 20 secs. | | |
| | | | Cold | | Broke in 20 secs. | | |
| | | | Cold | .5 Stu | Broke in 30 secs. | | |
| | | Camak | Cold | | Flow poor | 60+ | 95 |
| | | | Cold | | Flow excellent | 60+ | 95 |
| INDULIN MQK(e) | 1.7 | Sahuaro | 120°F | | Broke in 5 secs. | | |
| | | | 120°F | .5 Stu | Broke in 10 secs. | | |
| | | | Cold | | Broke in 20 secs. | | |
| | | | Cold | .5 Stu | Broke in 20 secs. | | |
| | | Camak | Cold | | Flow excellent | 60+ | 100 |
| | | | Cold | .5 Stu | Flow fair | 20 | 100 |

TABLE IV
(continued)

Evaluation of Cationic Slurry Seal Emulsifiers
Edgington Hard Base, pH 2.5; 64.0% Asphalt Content,
Camak and Sahuaro Aggregates

| Emulsifier | Mixing Performance[a] | | | | Comments | Set Time (min) | % Coating[c] |
| | % Dosage | Aggregate | Temperature | Additives[b] | | | |
|---|---|---|---|---|---|---|---|
| INDULIN MQK[e] - Molasses[d] (100:25) | 1.7 | Sahuaro | 120°F | | Broke in 10 secs. | | |
| | | | 120°F | .5 Stu | Broke in 10 secs. | | |
| | | | Cold | | Broke in 55 secs. | | |
| | | | Cold | .5 Stu | Broke in 25 secs. | | |
| | | Camak | Cold | | Flow excellent | 60+ | 55 |
| | | | Cold | .5 Stu | Flow excellent | | |
| Akzo Redicote 5762 | 1.7 | Sahuaro | 120°F | | Broke in 5 secs. | | |
| | | | 120°F | .5 Stu | Broke in 5 secs. | | |
| | | | Cold | | Broke in 5 secs. | | |
| | | | Cold | | Broke in 5 secs. | | |
| | | Camak | Cold | | Flow excellent | 60+ | 50 |
| | | | Cold | .5 Stu | Flow excellent | | |
| Akzo Redicote 4868 | 1.7 | Sahuaro | 120°F | | Broke in 5 secs. | | |
| | | | 120°F | .5 Stu | Broke in 5 secs. | | |
| | | | Cold | | Broke in 5 secs. | | |
| | | | Cold | .5 Stu | Broke in 5 secs. | | |
| | | Camak | Cold | | Flow excellent | 60+ | 50 |
| | | | Cold | .5 Stu | Flow excellent | 60+ | 50 |

TABLE IV
(continued)

Evaluation of Cationic Slurry Seal Emulsifiers
Edgington Hard Base, pH 2.5; 64.0% Asphalt Content,
Camak and Sahuaro Aggregates

| Emulsifier | % Dosage | Aggregate | Mixing Performance (a) Temperature | % Additives (b) | Comments | Set Time (min) | % Coating (c) |
|---|---|---|---|---|---|---|---|
| Akzo Redicote E-11 | 1.7 | Sahuaro | 120°F | | Broke in 5 secs. | | |
| | | | 120°F | .5 Stu | Broke in 5 secs. | | |
| | | | Cold | | Broke in 5 secs. | | |
| | | | Cold | | Broke in 5 secs. | | |
| | | Camak | Cold | | Flow excellent | 60+ | 95 |
| | | | Cold | | Flow excellent | 60+ | 95 | a) 100 parts aggregate, 10 parts water and 16 parts emulsion were used for the mixing experiments.
b) Based on the weight of aggregate, Stu: Stucco, Plaster of Paris, Ca-sulfate hemihydrate.
c) After boiling for 10 min. in water.
d) 80% solids in water; reacted five hours at 90°C.
e) 80% active.